United States Patent [19]

Higuchi et al.

[11] Patent Number: 4,464,363

[45] Date of Patent: Aug. 7, 1984

[54] AJUVANTS FOR RECTAL DELIVERY OF DRUG SUBSTANCES

[75] Inventors: Takeru Higuchi; Toshiaki Nishihata; Howard J. Rytting, all of Lawrence, Kans.

[73] Assignee: Merck & Co., Inc., Rahway, N.J.

[21] Appl. No.: 277,291

[22] Filed: Jun. 25, 1981

Related U.S. Application Data

[63] Continuation-in-part of Ser. No. 213,121, Dec. 5, 1980, abandoned, which is a continuation-in-part of Ser. No. 105,645, Dec. 20, 1979, abandoned.

[51] Int. Cl.³ ........................................... A61K 31/625
[52] U.S. Cl. ..................................................... 424/232
[58] Field of Search ......................................... 424/232

[56] References Cited

PUBLICATIONS

Chemical Abstracts, 83, 205953y, (1975), Toyoshima et al., Insulin Complex Salts with Aminobenzoate Derivatives.
Chemical Abstracts, 71, 89823g, (1969), Sugimoto, Isao Complexes XVI—Effect of Complex Formation on Drug Absorption etc.
Pharmaceutical Res. Laboratory, Yakugaku Zasshi, 88(5), 618–622, Studies on Complexes–Effect of Complex Formation on Drug Absorp. etc.
CA 69-65889 (17)—Complexes—Effect of Complex Formation on Drug Absorption from Alimentary Tract, Susimoto, Isao et al., Tanable Seiyaku Co. Ltd., Osaka, Yakusaku Zasshi V88F(6), pp. 690–694, (1968).
CA 69-50670(13), Complexes, Effect of Complex Formation Drug Absorption from Alimentary Tract, Susimoto, Issao, Tababe Seiyaku Co. Ltd., Japan Pharm. Bull. 16(6), pp. 1098–1104, (1968).
CA 69-94857(23) Complexes, Effect of Complex Formation on Drug Absorption from Alimentary Tract, Susimoto, Isao, Tanabe Seiyaku Co. Ltd., Pharm. Res. Chem. Bull. 16(8), pp. 1527–1532, (1968).
CA 71-33382(8) Complexes, Effect of Complex Formation on Drug Absorption from Alimentary Tract, Susimoto, Isao Tanabe Seiyaku Co. Ltd., Pharm. Res. Chem. Pharm. Bull., 17(5), pp. 994–998, (1969).
Shunji Ota Dept. Pharmacol. Showa Med. Col. Comments: Jap. 5 Pharm. 51, pp. 692–714, (1955), Influence of Various Substances on the Absorption of Histamine from the Large Intestine etc.
Microbiologic Pharmacologic Properties of New Ampicillin Deriv. etc., by Valcavi, R. Caponi et al.
Journal of Pharmaceutical Sciences, vol. 57, No. 8 (1968), Reuning et al., Effect of Complex Formation on Drug Absorption etc., pp. 1335–1341.
Journal American Pharm. Assoc. No. 9, pp. 527–530, Investigation of Complex Formed in Solution by Caffeine, Higuchi et al.

*Primary Examiner*—Stanley J. Friedman
*Attorney, Agent, or Firm*—Michael C. Sudol, Jr.; Manfred Polk

[57] ABSTRACT

A method and drug form for enhancing the rate of absorption of a rectally administered drug from the rectal compartment into the blood stream of a warm blooded animal. The method includes the steps of preparing a drug form capable of being rectally administered. The drug form comprises a therapeutically effective unit dosage amount of a selected drug of the type which is capable of being absorbed into the blood stream from the rectal compartment and hydroxy aryl or hydroxy aralkyl acids or salts, amides or esters thereof, the hydroxy aryl or hydroxy aralkyl acids or salts, amides or esters thereof being present in the drug form in a sufficient amount to be effective in enhancing the drug absorption rate, when rectally administering the drug form to warm blooded animals.

15 Claims, 7 Drawing Figures

Fig. 1

PER CENT ABSORPTION OF THEOPHYLLINE (-o-,-▲-) AFTER 1 HR FROM PERFUSATE IN THE RAT RECTUM UNDER SAME CONDITIONS. -o-; INITIAL CONCENTRATION = 0.2% SODIUM SALICYLATE AND 200 MG/ML THEOPHYLLINE, -▲-; INITIAL CONCENTRATION = 200 MG/ML THEOPHYLLINE, ONLY.

Fig. 3

1B. EFFECT OF pH AND SALICYLATE ON THE DISAPPEARANCE OF LIDOCAINE HCL FROM A PERFUSATE IN THE RAT RECTUM
o = 0.5% SODIUM SALICYLATE, • = NO SODIUM SALICYLATE.
INITIAL LIDOCAINE HCL CONCENTRATION WAS 500 MG/ML

Fig. 5. Gastric Acid Secretion Following Administration of Pentagastrin And Gastrin To The Anesthetized Rat.

Fig. 6. Plasma Profile Of Insulin And Glucose After Insulin Administration Intramuscularly And Rectally (Dog)

4,464,363

AJUVANTS FOR RECTAL DELIVERY OF DRUG SUBSTANCES

REFERENCE TO RELATED APPLICATION

This application is a continuation-in-part application of our co-pending application Ser. No. 213,121, filed Dec. 5, 1980 in the U.S. Patent and Trademark Office which itself was a continuation-in-part application of our application Ser. No. 105,645 filed Dec. 20, 1979 in the U.S. Patent and Trademark Office both are now abandoned.

BACKGROUND OF THE INVENTION

Field of the Invention and Description of the Prior Art

This invention relates to a method for administering drugs to warm blooded animals by rectal delivery and it particularly relates to a method for enhancing the rate of absorption of such rectally delivered drugs from the rectal compartment to the blood stream; this invention also relates to improved rectal suppository drug forms used in the practice of such method.

One known method of drug administration is accomplished by the incorporation of a drug in a "suppository", which generally speaking, is a medicated solid dosage form generally intended for use in the rectum, vagina, and to a lesser extent, in the urethra. Molded rectal suppositories usually employ vehicles that melt or soften at body temperatures so that the drug may be released for use. On the other hand, soft elastic gelatin capsule suppositories rely on the presence of moisture in the rectum which causes the capsule to open and release its liquid contents which contains its therapeutic agent. Drugs administered in suppository form are administered for either local or systemic effect. The action of the drug is dependent on the nature of the drug, its concentration, and its rate of absorption. Although rectal suppositories are commonly used for the treatment of constipation and hemorrhoids, that is, for local effect, such rectal suppositories are also administered rectally for systemic action. A wide variety of drugs may be rectally administered, as by the use of suppositories, including, for example, analgesics, antispasmodics, sedatives, tranquilizers, and antibacterial agents.

Rectal drug administration has many advantages over other routes of drug administration, such as oral administration and parenteral administration. For example, many drug substances that are given orally undergo inactivation in the stomach because of the acidic, enzymatic content of the stomach or the drug may be subject to digestive attack in the gut and/or to microbial degradation in the lower gut. Oral administration of drugs also directs all of the absorbed substances through the liver where they can be inactivated or reduced in effectiveness.

Rectal administration overcomes wholly, or in part, these known disadvantages of oral drug administration. Rectal drug administration also has advantages over parenteral administration. For example, rectal drug administration does not require highly trained personnel required for parenteral administration and also represents significantly less hazard to the patient.

In view of the known disadvantages or oral and parenteral drug administration, drug administration by rectal delivery enables many drugs to be absorbed from the anorectal area, and yet retain their therapeutic value. The lower hemorrhoidal vein, surrounding the colon and rectum, enters the inferior vena cava and thereby bypasses the liver. Therefore, drugs are absorbed directly into the general circulation when rectally administered. For further background on rectal delivery of drugs, reference is made herein to an article entitled "Rectal Administration of Drugs" by N. Senior, "Advances in Pharmaceutical Sciences", edited by Bean, Beckett, and Corlass, Volume IV, Academic Press (1974) and to Chapter 8, "Suppositories", by Joachim Anschel and Herbert A. Lieberman, Lachman and Lieberman "Theory and Practice of Industrial Pharmacy", Lea and Febiger (1976).

Despite the known advantages of rectal administration of drugs, the rectal administration of drugs is not totally without problems. First, many rectally administered drugs are poorly absorbed while others are slowly absorbed and, if so, are often inactivated or degraded while still in the rectal compartment. It would therefore be highly advantageous if rectally administered drug substances could have their rate of absorption from the rectal compartment to the blood stream enhanced.

SUMMARY OF THE INVENTION

It is therefore an important object of the present invention to provide a unique method for enhancing the absorption rate of rectally administered drugs from the rectal compartment to the blood stream.

It is also an object of the present invention to provide an improved rectal suppository drug form which enhances the absorption rate of rectally delivered drugs contained in a soft elastic gelatin capsule or a molded suppository.

It is a further important object of the present invention to provide an improved method for administering drugs by the use of rectal suppositories wherein enhanced absorption results from the incorporation of hydroxy aryl or hydroxy aralkyl acids or salts, amides or esters thereof into the drug formulation.

It is yet another important object of this invention to provide an improved rectal suppository having an enhanced absorption rate of a selected drug therefrom when in the rectal compartment, wherein hydroxy aryl or hydroxy aralkyl acids or salts, amides or esters thereof are incorporated into a drug formulation contained within a soft elastic gelatin capsule or molded type of rectal suppository.

Further purposes and objects of this invention will appear as the specification proceeds.

The foregoing objects are accomplished by providing a method and suppository drug form wherein the absorption rate of rectally administered drugs into the bloodstream of warm blooded animals is enhanced, the method comprising the steps of preparing a drug form capable of being rectally administered, the drug form comprising an effective unit dosage amount of a drug of a type which is capable of being absorbed from the rectal compartment into the blood stream and hydroxy aryl or hydroxy aralkyl acids or salts, amides or esters thereof, the hydroxy aryl or hyroxy aralkyl acids or salts, amides or esters thereof being present in said drug form in an amount sufficient to be effective in enhancing the absorption rate of a drug into the blood stream from the rectal compartment, and thereafter rectally administering the drug form to a warm blooded animal.

BRIEF DESCRIPTION OF THE DRAWINGS

Referring to the accompanying drawings, there is provided four graphs, to be hereinafter described in detail, illustrating the enhanced absorption rate of rectally administered drugs utilizing our improved rectal administration method and our improved rectal suppository drug form wherein.

DETAILED DESCRIPTION OF THE PREFERRED EMBODIMENTS

The present invention, generally, comprises the steps of preparing a drug form capable of being rectally administered, wherein the drug form comprises an effective unit dosage amount of a drug capable of being absorbed into the blood stream of a warm blooded animal from the rectal compartment and hyroxy aryl or hydroxy aralkyl acids or salts, amides or esters threof, the hydroxy aryl or hydroxy aralkyl acids or salts, amides or esters thereof being present in the drug form in a sufficient amount to be effective in enhancing the absorption rate, and rectally administering the drug form to the warm blooded animal.

Our method for enhancing the rate of absorption of drugs from the rectal compartment is useful for a wide range of drugs or drug categories including, but not limited to xanthines, anticancer agents, antibiotics (such as erythromycin, chloramphenicol and gentamycin), polypeptides and antiarrythmics (such as guinidine or lidocaine), all of which drugs are capable of being absorbed into the blood stream of a patient from the rectal compartment. Other specific drugs useful in the method and in combination with the hereinafter described adjuvants will be hereinafter identified. The amount of the drug used in our method for enhancing drug absorption varies over a wide range, generally any therapeutically effective unit dosage amount of the selected drug is used.

The hydroxy aryl or hydroxy aralkyl acids or salts, amides or esters thereof, that are used as the adjuvants in our method and in our suppositories, have the following structural formulae including the various isomers possible within the formulae set forth:

wherein $R_1$ is a radical selected from —$CO_2H$, —$(CH_2)_n$—COOH, —CH=CH—$CO_2H$, —$SO_3H$, —$CH_2SO_3H$, $X(CH_2)_nCO_2H$, $SO_2NHR_4$, PO(OH)N(OH)$_2$, PO(OH)OR$_4$, or a pharmaceutically acceptable salt thereof wherein $R_2$ is a radical selected from OH, H a lower alkoxy radical having 1–10 carbon atoms, a lower alkyl radical having 1–10 carbon atoms, a lower alkenyl radical having 2–5 carbon atoms, a lower alkanoyl radical having 1–5 carbon atoms, a carboxy radical, a carbo-lower alkoxy radical having 1–5 carbon atoms, a halo radical, a mono-, di-, or tri-halo lower alkyl radical having 1–5 carbon atoms, an amino radical, a mono- or di-lower alkyl amino radical having 1–5 carbon atoms, a carbamyl radical, a lower mono- or di-alkyl carbamyl radical wherein the alkyl group has 1–5 carbon atoms, a thio radical, a lower alkyl thio radical wherein the alkyl group has 1–5 carbon atoms, a cyano radical, a lower alkyl sulfone radical wherein the alkyl group has 1–5 carbon aoms, a lower alkyl sulfoxide radical wherein the alkyl group has 1–5 carbon atoms, a nitro radical, N(CN$_2$)$_2$, C(CN)$_3$, an alkynyl radical having 2–6 carbon atoms, a cycloalkyl radical having 3–10 carbon atoms, a cycloalkenyl radical having 3–10 carbon atoms, an aryl radical including phenyl, a hetroaryl radical including thiophenyl and imadazoalyl, or a heterocycloalkyl radical including morphilinyl and piperdinyl, wherein $R_3$ is a straight or branched alkyl radical having 1–6 carbon atoms or a hydroxy radical, wherein $R_4$ is H or a lower alkyl radical having 1–5 carbon atoms, wherein X is O or S, wherein n is an integer of 0–5, wherein y is 1 or 2, and when y is 2, both the $R_2$ radicals, taken together, can form a ring containing O, N or S.

More preferred adjuvants are those having the formula:

wherein $R_1$ is a radical selected from —$CO_2H$, —$(CH_2)$—COOH, —CH=CH—$CO_2H$, —$SO_3H$, —$CH_2SO_3H$, or O($CH_2$) $CO_2H$ or a pharmaceutically acceptable salt thereof wherein $R_2$ is selected from OH, H, a lower alkoxy radical having 1–10 carbon atoms, a lower alkyl radical having 1–10 carbon atoms, a halo radical, a mono-, di-, or tri-halo lower alkyl radical wherein the alkyl group has 1–5 carbon atoms, a lower alkyl thio radical wherein the alkyl radical has 1–5 carbon atoms, a cycloalkyl radical having 3-10 carbon atoms, or a cycloalkenyl radical having 3-10 carbon atoms and wherein y is an integer of 1 or 2.

Highly preferred adjuvants are those having the formula:

wherein $R_1$ is $CO_2H$, $-(CH_2)-COOH$, or $SO_3H$, or a pharmaceutically acceptable salt thereof wherein $R_2$ is OH, H, a lower alkoxy radical, including methoxy, ethoxy, butoxy, or octyloxy, a lower alkyl radical including methyl, isopropyl, ethyl, t-butyl, n-butyl, or t-octyl, a halo radical, or a tri-halo lower alkyl radical including trifluoromethyl, and wherein y is an integer of 1 or 2.

Specific adjuvants useful in our method and drug form include salicylic acid, 5-methoxysalicylic acid, 3,4-dihydroxyphenylacetic acid (DOPAC) and homovanillic acid and their sodium salts thereof.

It is most highly preferred that the drugs combined with the adjuvants in our invention be drugs that do not form a complex with the adjuvant. By complex is meant a chemical combination of the drug and adjuvant that is distinct from a physical combination or a mere admixture.

As in the case of the drugs used in our method and suppositories, the amount of adjuvant used may vary over a wide range; in general, the identity and the amount of the adjuvant used in connection with the drug are selected in order to be effective in enhancing the absorption rate of the drug from the rectal compartment into the bloodstream. Generally the amount of adjuvant in our drug forms (suppositories) is from 100–1000 mg in each unit dose. The percentage of adjuvant in the total combination of drug plus adjuvant is 20–95% with a preferred ratio of adjuvant in the total combination of adjuvant plus drug being 30–60%. A most preferred ratio of adjuvant to adjuvant plus drug is 50%.

The particular method used for the rectal administration of the drug and the adjuvant is preferably by use of the appropriate size, shape or form of any of the various types of rectal suppositories known to the pharmaceutical art; alternatively, the drug may be administered with the adjuvant by means of microenema. Useful rectal suppositories with which the present method may be used include cocoa butter suppositories, synthetic fat suppositories, and gelatin capsules including soft elastic gelatin capsule type suppositories as well as other controlled release devices such as an osmotic pump or other polymeric devices.

A preferred form of suppository comprises a soft elastic gelatin capsule having an outer shell which encloses the drug and the adjuvant in a suitable vehicle which will not attack the walls of the seamless gelatin capsule. The shell encapsulates a preselected drug form and the adjuvant. The gelatin capsule shell may be formulated in accordance with conventional techniques for making filled, seamless, soft elastic gelatin capsules containing therapeutically effective unit dosage amounts of the active drug ingredient. For example, one conventional shell formulation includes about 30–53 parts by weight of gelatin, 15–48 parts by weight of a plasticizer, such as glycerine or sorbitol, and about 16–40 parts by weight of water. Additionally, the gelatin shell may contain preservatives such as mixed parabens, ordinarily methyl or propyl parabens in about a 4:1 ratio. The parabens may be incorporated in the shell formulation in minor proportions as compared to the total weight of the shell formulation. Conventional gelatin capsules utilize gelatin having a bloom value of about 160–200 although this amount may be varied.

In a conventional manner, the gelatin composition is mixed and melted under vacuum conditions. The capsules may be simultaneously formed and filled using a conventional method and apparatus such as disclosed, for example, in U.S. Pat. Nos., 1,970,396; 2,288,327; and 2,318,718. The gelatin capsules are formed into a desired shape and size for insertion into the rectal compartment. It is to be understood, however, that the particular method used for making the soft elastic gelatin shell and for incorporating the fill therein are not considered part of the invention herein.

One of the more important uses of our method and suppository for rectal administration of drugs is in the administration of sustained release or programmed release drug forms which will slowly release the drug substances into the rectal compartment of a warm blooded animal. The present method and suppository permit the rapid clearance of the released drug into the blood stream by way of the lower hemorrhoidal vein, instead of moving upwards into the lower gut. This technique thereby reduces or avoids loss of drug effectiveness associated with passage of the drug through the liver.

The following data sets forth specific experiments illustrating various embodiments of the present invention.

EXAMPLE I

Figure 1:
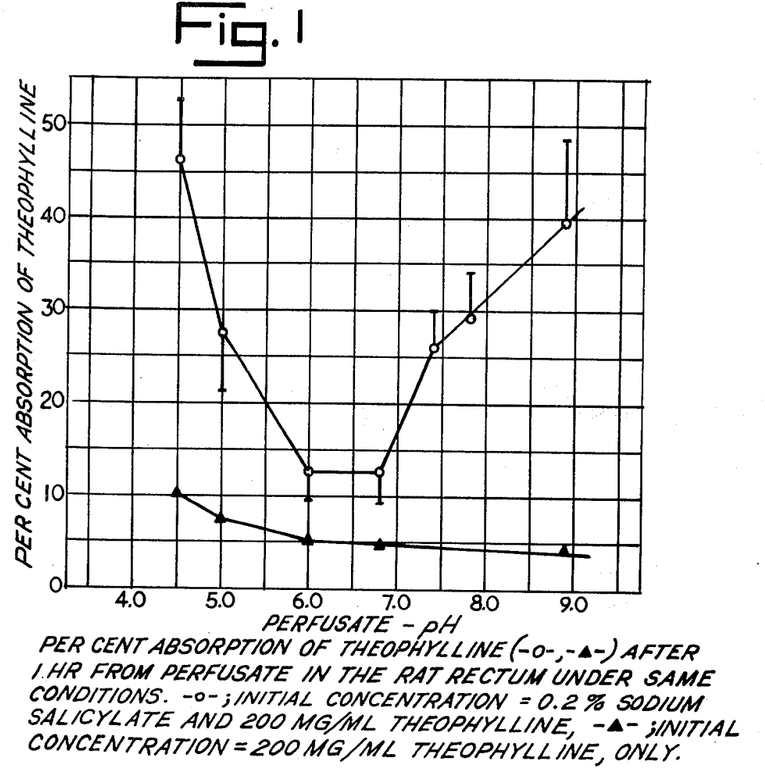
FIG. 1 is a graph illustrating the enhanced absorption rate of theophylline by using our method.

Referring to the accompanying graphs, the effect of salicylic acid on the relative rate of absorption of theophylline from the rectal compartment of a rat is shown in FIG. 1. In this experiment, the amount of remaining theophylline, originally at a concentration of about 200 mg/ml, in aqueous solution and continually recirculated or perfused to the rectal compartment of the rat, at the end of one hour, is shown as the lower plot for studies carried out in the presence of 0.2% sodium salicylate, is shown as the upper plot. It is clear that the addition of the salicylate has a marked effect on the rate of absorption of the theophylline into the animal, the adjuvant effect being greatest below a pH of 5.5 and above a pH of 7.5.

Figures 2, 4:
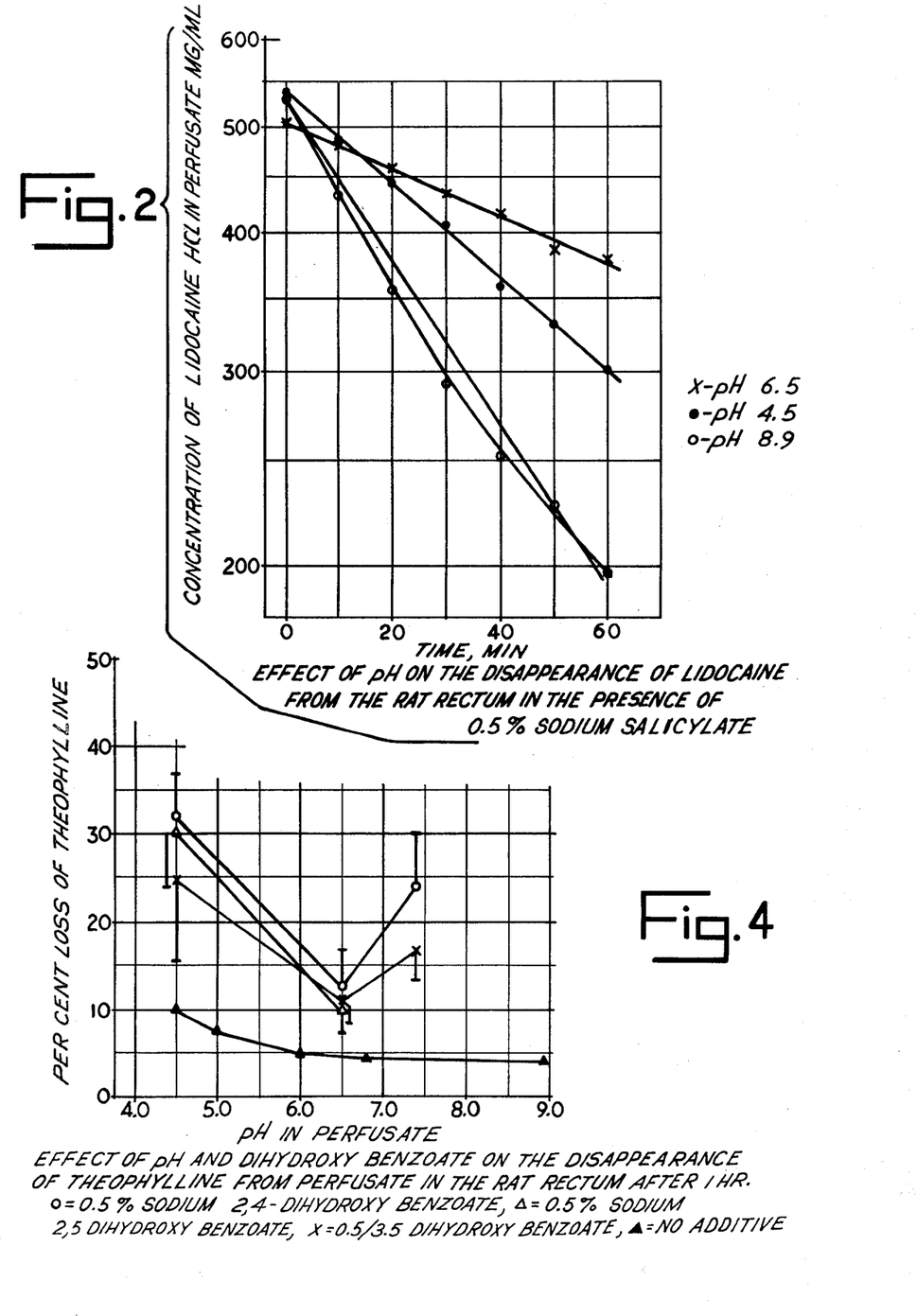
FIG. 2 is a graph illustrating the enhanced absorption rate of lidocaine HCL when using our method.
FIG. 4 is another graph illustrating enhanced absorbtion rate of theophylline by rectal administration when utilizing our improved method.
Figure 3:
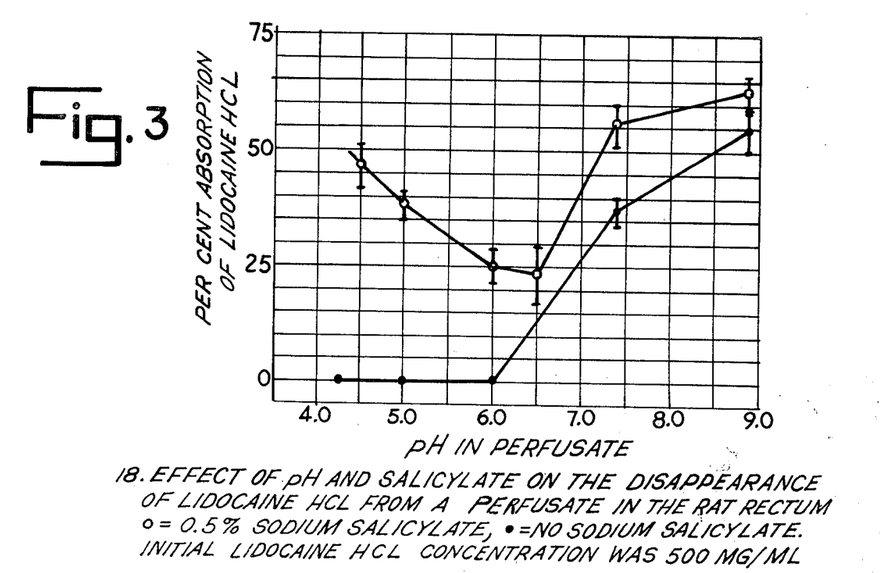
FIG. 3 is another graph illustrating the enhancement of the absorption rate of lidocaine HCL from the rectal compartment while utilizing our improved method.

A similar accelerating effect on the absorption of the antiarrythmic drug lidocaine by sodium salicylate is evident from FIGS. 2 and 3 where the amount of the drug absorbed is shown against time and pH. For this drug, the effect of the hydroxyaromatic carboxylate is particularly evident below a pH of 7.0. In fact, below a pH of 6.0, the rate of absorption of the drug by itself approaches zero, whereas in the presence of the salicylate or its acidic form, the absorption rate is substantial and appears to increase at the lower pH values.

With reference to FIG. 4, the adjuvant effect on the rectal absorption of these drugs is not limited to salicylic acid alone but is general for the disclosed adjuvants. This adjuvant effect is evident for data obtained for several resorcylic acids and gentisic acid.

EXAMPLE II

The ability of various of the adjuvants of the present invention to enhance the rate of absorption of significant drugs which are rectally administered, from the rectal compartment into the blood stream, is demonstrated with an in situ perfusion mehod of the rectum. The rectum of a male Sprague-Dowley rat weighing 275–300 g., is exposed by an abdominal incision, a glass cannula is inserted into the distal direction and tied firmly to keep it in position. A second cannula is inserted through the anus 1 cm. inside the rectum and secured by ligation. Thus, about 2 cm. of the rectum is exposed to the perfusate. The perfusate (6 ml.) is circulated at a rate of 2 ml./min. at 38° C. As perfusate, 1/15M—phosphate buffer solutions are used and the ionic strength of the perfusate is adjusted to 0.75 with sodiumchloride as necessary. The adjuvant is employed at a concentration of 0.5%, while the concentration of the various drugs is varied in accordance with the known effective dosages for said drugs. The amount of drug remaining in the perfusate is analyzed as a function of time by appropriate methods, e.g., by high-pressure liquid chromatography. Blood levels are also measured in blood samples taken from a vein in the leg of the rat. The results of this method show that the percent absorption of the various drugs after 1 hour from the perfusate in the rat rectum is significantly enhanced by the presence of an adjuvant of the present invention.

Following is a table of drug and adjuvant combinations which are evaluated in accordance with the method described above:

| Drug | Adjuvant |
| --- | --- |
| 1. 3,5-diamino-N—(aminoiminomethyl)-6-chloropyrazinecarboxamide (amiloride); | sodium salicylate |
| 2. 6-chloro-3,4-dihydro-2H—1,2,4-benzothiadiazine-7-sulfonamide-1,1-dioxide (hydrochlorothiazide); | sodium homovanillate |
| 3. amiloride hydrochloride and hydrochlorothiazide (moduretic); | 2,5-dihydroxy benzoate |
| 4. S—α-hydrozino-3,4-dihydroxy-α-methylbenzenepropanoic acid monohydrate (carbidopa); | sodium 5-methoxy salicylate |
| 5. carbidopa and 3-hydroxy-L-tyrosine (levodopa) (Sinemet); | sodium 3-methoxy salicylate |
| 6. pentagastrin | sodium salicylate |
| 7. 3-(5H—dibenzo[a,d]cyclohepten-5-ylidene)-N,N—dimethyl-1-propanamine (cyclobenzaprine); | 2,5-dihydroxy benzoate |
| 8. 2',4'-difluoro-4-hydroxy-[1,1'-biphenyl]-3-carboxylic acid (diflunisal); | sodium homovanillate |
| 9. 1-(p-chlorobenzoyl)-5-methoxy-2-methylindole-3-acetic acid (indomethacin); | sodium homovanillate |
| 10. 3-hydroxy-α-methyl-L-tyrosine (methyldopa); | sodium salicylate |
| 11. (Z)-5-fluoro-2-methyl-1-[[4-(methylsulfinyl)phenyl]methylene]-1H—indene-3-acetic acid (sulindac)' | sodium 5-methoxy salicylate |
| 12. S—(—)-1-(tert-butylamino)-3-[(4-morpholino-1,2,5-thiadiazol-3-yl)oxy]-2-propanol(timolol); | sodium salicylate |
| 13. (—)-1-(cyclopropylmethyl)-4-[3-(trifluoromethylthio)-5H—dibenzo(a,d) cyclohepten-5-ylidene]piperidine hydrochloride | sodium salicylate |
| 14. N—[(S)—1-(ethoxycarbonyl)-3-phenylpropyl]-L-alanyl-L-proline maleate | sodium homovanillate |
| 15. (+)10,11-dihydro-5-methyl-5H—dibenzo[a,d] cyclohepten-5,10-imine oxalate | 2,5-dihydroxy benzoate |
| 16. 1-ethyl-6-fluoro-1,4-dihydro-4-oxo-7-(1-piperazinyl)-3-quinolinecarboxylic acid | sodium 5-methoxy salicylate |
| 17. 3-fluoro-D-alanine and D-4-(1-methyl-3-oxo-1-butenylamino)-3-isoxazolidinone sodium salt hemihydrate | sodium 3-methoxy salicylate |
| 18. L-N—(2-oxopiperidin-6-yl-carbonyl)-histidyl-L-thiazolidine-4-carboxamide | sodium salicylate |
| 19. gastrin | 2,5-dihydroxy benzoate |
| 20. (6,7-dichloro-2-methyl-2-phenyl-1-oxo-5-indanyloxy) acetic acid | sodium homovanillate |
| 21. αmethyl-4-(2-methylpropyl) benzeneacetic acid (ibuprofen) | sodium homovanillate |
| 22. (+)-6-methoxy-α-methyl-2-naphthaleneacetic acid (naproxen) | sodium salicylate |
| 23. 5-(4-chlorobenzoyl)-1.4-dimethyl-1H—pyrrole-2-acetic acid | sodium 5-methoxy salicylate |
| 24. 4-butyl-1,2-diphenyl-3,5-pyrazolidinedione (phenylbutazone) | sodium salicylate |
| 25. 9-fluoro-11β,17,21-trihydroxy-16α-methylpregna-1,4-diene-3,20-dione (dexamethasone) | sodium salicylate |
| 26. 11β,17,21-trihydroxypregna-1,4-diene-3,20-dione (prednisolone) | sodium homovanillate |
| 27. 2-(2,6-dichloroanilino)-2-imidazoline (clonidine) | 2,5-dihydroxy benzoate |
| 28. 1-(isopropylamino)-3-(1-naphthyloxy)-2-propanol (propranolol) | sodium 5-methoxy salicylate |
| 29. 7-chloro-1,3-dihydro-1-methyl-5-phenyl-2H—1,4-benzodiazepin-2-one (diazepam) | sodium 3-methoxy salicylate |
| 30. 7-chloro-N—methyl-5-phenyl-3H—1,4-benzodiazepin-2-amine 4-oxide (chlorodiazepoxide) | sodium salicylate |
| 31. 5-(aminosulfonyl)-4-chloro-2-[(2-furanylmethyl)amino]benzoic acid (furosemide) | 2,5-dihydroxy benzoate |
| 32. insulin | sodium homovanillate |
| 33. 1-ethyl-1,4-dihydro-7-methyl-4-oxo-1,8-naphthyridine-3-carboxylic acid (nalidixic acid) | sodium homovanillate |
| 34. gentamycin | sodium salicylate |
| 35. 4-[4-(4-chlorophenyl)-4-hydroxy-1-piperidinyl]-1-(4-fluorophenyl)-1-butanone (haloperidol) | sodium 5-methoxy salicylate |
| 36. 1-(3-mercapto-2-methyl-1-oxopropyl)-L-proline (captopril) | sodium salicylate |
| 37. N (1) (S)—ethoxycarbonyl-3-phenyl propyl-1-alanyl-L-proline maleate (MK421) | sodium salicylate |

As already described, the method of the present invention for enhancing the rate of absorption of drugs from the rectal compartment is useful for a wide range of drugs. Without limiting the broad applicability of the novel method, there is also pointed out below a number of drugs for which the novel method is particularly useful, thus comprising preferred embodiments of the present invention:

3,5-diamino-N-(aminoiminomethyl)-6-chloropyrazine-carboxamide (amiloride);
6-chloro-3,4-dihydro-2H-1,24-benzothiadiazine-7-sulfonamide-1,1-dioxide (hydrochlorothiazide);
amiloride hydrochloride and hydrochlorothiazide (Moduretic);
S-α-hydrozino-3,4-dihydroxy-α-methylbenzene-propanoic acid monohydrate (carbidopa);
carbidopa and 3-hydroxy-L-tyrosine (levodopa) (Sinemet);
heparin
3-(5H-dibenzo[a,d]cyclohepten-5-ylidene)-N,N-dimethyl-1-propanamine (cyclobenzaprine);
2′,4′-difluoro-4-hydroxyl[1,1′-biphenyl]-3-carboxylic acid (diflunisal);
1-(p-chlorobenzoyl)-5-methoxy-2-methylindole-3-acetic acid (indomethacin);
3-hydroxy-α-methyl-L-tyrosine (methyldopa); (Z)-5-fluoro-2-methyl-1-[[4-(methylsulfinyl)phenyl]methylene]-1H-indene-3-acetic aid (sulindac);
S-(−)-1-(tert-butylamino)-3-[(4-morpholino-1,2,5-thiadiazol-3-yl)oxy]-2-propanol (timolol);
(−)-1-(cyclopropylmethyl)-4-[3-(trifluoromethylthio)-5H-dibenzo (a,d) cyclohepten-5-ylidene]piperidine hydrochloride
N-[(S)-1(ethoxycarbonyl)-3-phenylpropyl]-L-alanyl-L-proline maleate
(+)10,11-dihydro-5-methyl-5H-dibenzo[a,d]cyclohepten-5,10-imine oxalate
1-ethyl-6-fluoro-1,4-dihydro-4-oxo-7-(1-piperazinyl)-3-quinolinecarboxylic acid
3-fluoro-D-alaine and D-4-(1-methyl-3-oxo-1-butenylamino)-3-isoxazolidinone sodium salt hemihydrate
L-N-(2-oxopiperidine-6-ylcarbonyl)-histidyl-L-thiazolidine-4-carboxamide
gentamycin
(6,7-dichloro-2-methyl-2-phenyl-1-oxo-5-indanyloxy)acetic acid
α-methyl-4-(2-methylpropyl)benzeneacetic acid(ibuprofen) (+)-6-methoxy-α-methyl-2-naphthaleneacetic acid(naproxen) 5-(4-chlorobenzoyl)-1,4-dimethyl-1H-pyrrole-2-acetic acid 4-butyl-1,2-diphenyl-3,5-pyrazolidinedione (phenylbutazone)
9-fluoro-11β,17,21-trihydroxy-16α-methylpregna-1,4-diene-3,20-dione (dexamethasone)
11β,17,21,trihydroxypregna-1,4-diene-3,20-dione (prednisolone)
2-(2,6-dichloroanilino)-2-imidazoline (clonidine)
1-(isopropylamino)-3-(1-naphthyloxy)-2-propanol (propranolol)
7-chloro-1,3-dihydro-1-methyl-5-phenyl-2H-1,4-benzodiazepin-2-one (diazepam)
7-chloro-N-methyl-5-phenyl-3H-1,4-benzodiazepin-2-amine 4-oxide (chlordiazepoxide)
5-(aminosulfonyl)-4-chloro-2-[(2-furanylmethyl)amino]-benzoic acid (furosemide)
erythromycin
1-ethyl-1,4-dihydro-7-methyl-4-oxo-1,8-naphthyridine-3-carboxylic acid (nalidixic acid)
gastrin or pentagastrin
4-[4-(4-chlorophenyl)-4-hydroxy-1-piperidinyl[-1-(4-fluorophenyl)-1-butanone (haloperidol)
1-(3-mercapto-2-methyl-1-oxopropyl)-L-proline (captopril)
N(1) (S)-ethoxycarbonyl-3-phenyl sodium salicylate propyl-1-alanyl-L-proline maleate (MK 421)

EXAMPLE III

A suppository suitable for human use is prepared using the following ingredients:

| Ingredient | Amount |
| --- | --- |
| A. Sodium 5-methoxy salicylate | 500 mg. |
| B. Gentamycin | 1 g. |
| C. Witepsol$^R$H-15 suppository excipient[1] [glycerol esters of mixtures of saturated vegetable fatty acids, predominantly lauric acid, derived from purified, specially selected coconut palm kernels, by separation into fatty acid and glyceride portions, fractional distillation of the fatty acid portion, followed by hydrogenation and esterification with glycerin.] | 1.5 g. |

[1]Available from Dynamit-Nobel Chemicals, A.G., Troisdorf-Oberlar, Germany.

Dry ingredients A and B are ground together to form a well-mixed, fine powder. Separately, ingredient C is heated to 40°–50° C. till fluid, after which it is mixed with the fine powder mixture of A and B and poured into a mold to form a unit dosage suppository.

In like manner, the following amounts of various drugs may be incorporated into supositories using the same excipient and adjuvant and preparation technique described above:

| Drug | Amount |
| --- | --- |
| hydrochlorothiazide | 75 mg. |
| Sinemet (carbidopa and levodopa) | 50/200 mg. |
| cyclobenzaprine | 10 mg. |
| diflunisal | 250 mg. |
| indomethacin | 75 mg. |
| methyldopa | 500 mg. |
| sulindac | 200 mg. |
| ibuprofen | 600 mg. |
| naproxen | 250 mg. |
| phenylbutazone | 100 mg. |
| dexamethasone | 4 mg. |
| prednisolone | 25 mg. |
| clonidine | 0.1 mg. |
| propranolol | 40 mg. |
| diazepam | 5 mg. |
| chlorodiazepoxide | 5 mg. |
| furosemide | 60 mg. |
| pentagastrin orgactrin | 1000 mg. |
| nalidixic acid | 1000 mg. |
| insulin | 500 mg. |
| haloperidol | 3 mg. |
| captopril | 150 mg. |
| timolol | 25 mg. |
| (−)-1-(cyclopropylmethyl)-4-[3-(trifluoromethylthio)-5H—dibenzo(a,d)cyclohepten-5-ylidene]piperidine hydrochloride | 30 mg. |
| N—[(S)—1-(ethoxycarbonyl)-3-phenylpropyl]-L-alanyl-L-proline maleate | 25 mg. |
| (+)10,11-dihydro-5-methyl-5H—dibenzo[a,d]cyclohepten-5-,10-imine oxalate | 3 mg. |
| 1-ethyl-6-fluoro-1,4-dihydro-4-oxo-7-(1-piperazinyl)-3-quinolinecarboxylic acid | 200 mg. |
| 3-fluoro-D-alanine and D-4-(1- | 500 mg./1500 mg. |

-continued

| Drug | Amount |
| --- | --- |
| methyl-3-oxo-1-butenylamino)-3-isoxazolidinone sodium salt hemihydrate | |
| L-N—(2-oxopiperidin-6-yl-carbonyl)-histidyl-L-thiazolidine-4-carboxamide | 2 mg. |
| heparin | 500 mg. |
| N(1) (S)—ethoxycarbonyl-3-phenylpropyl-1-alanyl-L-proline maleate (MK-421) | 150 mg. |
| (6,7-dichloro-2-methyl-2-phenyl-1-oxo-5-indanyloxy) acetic acid | 100 mg. |
| gentamycin | 100 mg. |
| erythromycin | 100 mg. |

The adjuvants may be chosen from the following salts of their acids.
Sodium 5-methoxysalicylate
Sodium salicylate
Sodium homovanilate
Sodium 2,5-dihydroxybenzoate
Sodium 2,4-dihydroxybenzoate
Sodium 3,4-dihydroxymandelate
Sodium 3-methoxy-4-hydroxymandelate
Sodium 3-methoxy-4-hydroxycinnamate
Sodium 5-methoxy-2-hydroxyphenylsulfonate
Sodium 3-methylsalicylate
Sodium 5-methylsalicylate
Sodium 5-tert-octylsalicylate
Sodium 3-tert-butyl-6-methylsalicylate
Sodium 3,5-diisopropylsalicylate
Sodium 3-tert-butyl-5-methylsalicylate
Sodium guaicolsulfonate
Sodium 5-bromosalicylate
Sodium 3,5-dibromosalicylate
Sodium 5-iodosalicylate
Sodium 3,5-dibromosalicylate
Sodium 2-hydroxyphenylacetate
Sodium 3-hydroxy-2-naphthoate
Sodium mandelate
Sodium phenyllactate
Sodium 2-hydroxyphenylmethanesulfonate
Sodium 5-trifluoromethyl-2-hydroxybenzoate
Sodium 4-hydroxy-3-hydroxyphenylmethanesulfonate
Sodium 3-methoxysalicyalte
Sodium 5-octyloxysalicylate
Sodium 5-butoxysalicylate
Sodium p-hydroxyphenoxyacetate
Sodium 3,4-dihydroxyphenylacetate
Sodium 5-chlorosalicylate
Sodium 3,4-dihydroxycinnamate
Sodium 3,5-dihydroxybenzoate
Sodium 2-hydroxy-3-methoxybenzoate
Sodium 1-hydroxy-2-naphthoate
Sodium salicylurate

EXAMPLE IV

The ability of various of the adjuvants of the present invention to enhance the rate of absorption of significant drugs which are rectally administered, from the rectal compartment into the blood stream, is demonstrated with an in situ perfusion method of the rectum. The rectum of a male Sprague-Dawley rat weighing 275–300 g., is exposed by an abdominal incision, a glass cannula is inserted in the distal direction and tied firmly to keep it in position. A second cannula is inserted through the anus 1 cm. inside the rectum and secured by ligation. Thus, about 2 cm. of the rectum is exposed to the perfusate. The perfusate (6 ml.) is circulated at a rate of 2 ml./min. at 38° C. As perfusate, 1/15M—phosphate buffer solutions are used and the ionic strength of the perfusate is adjusted to 0.75 with sodium chloride as necessary. The hydroxyaromatic acid adjuvant is employed at a concentration of 0.5%, while the concentration of the various drugs is varied in accordance with the known effective dosages for said drugs. The amount of drug remaining in the perfusate is analyzed as a function of time by appropriate methods, e.g. by high-pressure liquid chromatography. Blood levels are also measured by blood samples taken from a vein in the leg of the rat. The results of this method show that the percent absorption of the various drugs after 1 hour from the perfusate in the rat rectum is significantly enhanced by the presence of the adjuvant of the present invention. Following is a table of drug and adjuvant combinations which are evaluated in accordance with the method described above:

| | | |
| --- | --- | --- |
| 1. | 3,7-Dihydro-1,3-dimethyl-1H—purine-2,6-dione (theophylline); | Sodium salicylate, sodium benzoate, sodium o-anisate, sodium p-anisate, sodium 3-methoxy salicylate, sodium 2,4-dihydroxy benzoate sodium 2,5-dihydroxy benzoate, sodium 3,5-dihydroxy benzoate sodium 2,4-dimethoxy benzoate sodium homovanillate sodium 5-methoxy salicylate |
| 2. | 2-(Diethylamino)-N—(2,6-dimethyl-phenyl) acetamide (lidocaine); | Sodium salicylate, sodium benzoate, sodium o-anisate sodium p-anisate, sodium 3-methoxy salicylate, sodium 2,4-dihydroxy benzoate sodium 2,5-dihydroxy benzoate, sodium 3,5-dihydroxy benzoate sodium 2,4-dimethoxy benzoate sodium homovanillate sodium 5-methoxy salicylate |
| 3. | 3-hydroxy-L-tyrosine (levodopa), (L-Dopa); | Sodium salicylate, sodium benzoate, sodium o-anisate, sodium p-anisate, sodium 3-methoxy salicylate, sodium 2,4-dihydroxy benzoate sodium 2,5-dihydroxy benzoate, sodium 3,5-dihydroxy benzoate sodium 2,4-dimethoxy benzoate sodium homovanillate sodium 5-methoxy salicylate |
| 4. | Gentamycin | Sodium salicylate, sodium benzoate, sodium o-anisate, sodium p-anisate, sodium 3-methoxy salicylate, |

| | -continued |
|---|---|
| | sodium 2,4-dihydroxy benzoate |
| | sodium 2,5-dihydroxy benzoate, |
| | sodium 3,5-dihydroxy benzoate |
| | sodium 2,4-dimethoxy benzoate |
| | sodium homovanillate |
| | sodium 5-methoxy salicylate |

EXAMPLE V

The ability of various of the hydroxyaromatic acid adjuvants of the present invention to enhance the rate of absorption of significant drugs which are rectally administered, from the rectal compartment into the blood stream, is also demonstrated with an in vivo absorption method of the rectum. The rectum of male Sprague-Dawley rat weighing 275–300 g., is exposed by an abdominal incision. A 0.3 ml. sample of the drug solution is injected into a 2 cm. section of the rectum and the drug solution is maintained in that section by ligating the rectum with thread. Alternatively, 0.3 ml. of the drug solution is injected into the rectum using a cannula and the anus is tied firmly to prevent leakage of the drug solution. The hydroxyaromatic acid adjuvant is employed at a concentration of 0.5%, while the concentration of the various drugs is varied in accordance with the known effective dosages for said drugs. The amount of drug present in the blood is analyzed as a function of time by extraction with ether at a pH of less than 2.0 after deproteinization with a 3% trichloroacetic acid solution. Following centrifugation, the ether layer is evaporated and the sediment is dissolved in methanol. This methanol sample containing the drug is assayed by high-pressure liquid chromatography. Blood levels are also measured in blood samples taken from a vein in the leg of the rat using a cannula.

The results of this method show that the percent absorption of the various drugs after one hour in the blood stream is significantly enhanced by the presence of the hydroxyaromatic acid adjuvant of the present invention. Following is a table of drug and adjuvant combinations which are evaluated in accordance with the method described above:

| 1. 3,7-Dihydro-1,3-dimethyl-1H—purine-2,6-dione (theophylline); | Sodium salicylate, sodium benzoate, sodium o-anisate, sodium p-anisate, sodium 3-methoxy salicylate, sodium 2,4-dihydroxy benzoate sodium 2,5-dihydroxy benzoate, sodium 3,5-dihydroxy benzoate sodium 2,4-dimethoxy benzoate sodium homovanillate sodium 5-methoxy salicylate |
|---|---|
| 2. 2-(Diethylamino)-N—(2,6-dimethyl-phenyl) acetamide (lidocaine); | Sodium salicylate, sodium benzoate, sodium o-anisate sodium p-anisate, sodium 3-methoxy salicylate, |

| | -continued |
|---|---|
| | sodium 2,4-dihydroxy benzoate |
| | sodium 2,5-dihydroxy benzoate, |
| | sodium 3,5-dihydroxy benzoate |
| | sodium 2,4-dimethoxy benzoate |
| | sodium homovanillate |
| | sodium 5-methoxy salicylate |
| 3. 3-hydroxy-L-tyrosine (levodopa), (L-Dopa); | Sodium salicylate, sodium benzoate, sodium o-anisate, sodium p-anisate, sodium 3-methoxy salicylate, sodium 2,4-dihydroxy benzoate sodium 2,5-dihydroxy benzoate, sodium 3,5-dihyroxy benzoate sodium 2,4-dimethoxy benzoate sodium homovanillate sodium 5-methoxy salicylate |
| 4. Gastin or pentagastrin | Sodium salicylate, sodium benzoate, sodium o-anisate, sodium p-anisate, sodium 3-methoxy salicylate, sodium 2,4-dihydroxy benzoate sodium 2,5-dihydroxy benzoate, sodium 3,5-dihydroxy benzoate sodium 2,4-dimethoxy benzoate sodium homovanillate sodium 5-methoxy salicylate |

EXAMPLE VI

The ability of various of the adjuvants of the present invention to enhance the rate of absorption of insulin which is rectally administered, from the rectal compartment into the blood stream, is demonstrated with a microenema technique. Insulin is administered to a male Sprague-Dawley rat weighing 275–300 g. using a microenema. The microenema is prepared with 0.2M phosphate buffer, pH 5.0. A volume of 0.3 ml. is delivered rectally. Blood samples are taken from a jugular vein of the rat at designated time intervals. The 0.3 ml. microenema consists of 5 mg. of adjuvant and 1.8 I.U. of insulin. Plasma levels of glucose are measured using the ortho-toluidine method. The results of this method show that plasma glucose levels decrease rapidly after administration of the insulin microenema in the presence of adjuvant. The plasma glucose levels gradually recover from 60 to 120 minutes after administration. The adjuvant greatly enhanced the rectal absorption of insulin. The following is a table of drug and adjuvant combinations which are evaluated in accordance with the method described above:

| Drug | Adjuvant |
|---|---|
| Insulin | Sodium salicylate, sodium 5-methoxy salicylate, |

| Drug | Adjuvant |
|---|---|
| | sodium 3-methoxy salicylate, sodium homovanillate |

EXAMPLE VII

The ability of various of the adjuvants of the present invention to enhance the rate of absorption of heparin which is rectally administered, from the rectal compartment into the blood stream, is demonstrated using a microenema technique. A male Sprague-Dawley rat receives 1000 units of heparin (Na salt) dissolved in a 0.1 ml aqueous microenema also containing 20 mg. of absorption adjuvant. The results of this method show that there is a dramatic increase in clotting time after rectal administration of heparin with adjuvant. Clotting times were greater than 90 minutes in blood samples taken at 15 minutes through 90 minutes. Following is a table of drug and adjuvant combinations which are evaluated in accordance with the method described above:

| Drug | Adjuvant |
|---|---|
| Heparin | Sodium salicylate, sodium 5-methoxy salicylate, sodium 3-methoxy salicylate, sodium homovanillate |
| MK-421 | Sodium salicylate, sodium 5-methoxy salicylate, sodium homovanillate |

EXAMPLE VIII

The ability of various of the adjuvants of the present invention to enhance the lymphatic transport of water soluble drugs after rectal administration in conjunction with salicylate-based absorption adjuvants is demonstrated with a microenema technique. A male Sprague-Dawley rat weighing 200-225 g. is anesthetized with pentobarbital and the thoracic duct is cannulated. Flow through this duct includes the mesenteric drainage. Drugs and absorption adjuvants are delivered in the form of a 0.2 ml. aqueous microenema 1/15M phosphate buffer, at a pH 7.4 (for insulin a pH 5.0). Blood samples (0.3 ml) are taken from the external jugular vein of the rat and centrifuged at 2000 rpm for ten minutes to collect plasma. With the exception of phenol red, determination of drug concentration in plasma and lymph is carried out using a high-pressure liquid chromatography technique at 254 nm. Plasma and lymph samples are deproteinized with acetonitrile. Phenol red is determined at 540 nm after adding 1.0N sodium hydroxide to the plasma or lymphatic samples. Insulin is assayed with an immunospecific enzyme assay kit supplied by Toyo Jozo Ltd., Japan. The results of this method show that the absorption of the drug in plasma and in lymph collected from the thoracic duct is significantly enhanced by the presence of the hydroxyaromatic acid adjuvant of the present invention. Following is a table of drug and adjuvant combinations which are evaluated in accordance with the method described above:

| Drug | Adjuvant |
|---|---|
| 1. 4,4'-(3H—2,1-Benzoxathiol-3-ylidene)bisphenol S,S—dioxide (phenol red); | Sodium 5-methoxy salicylate, sodium salicylate |
| 2. Insulin | Sodium 5-methoxy salicylate, sodium salicylate |
| 3. 3,7-Dihydro-1,3-dimethyl-1H—purine-2,6-dione (theophylline) | Sodium 5-methoxy salicylate, sodium salicylate |

EXAMPLE IX

The ability of various of the dipeptide and metabolites of epinephrine adjuvants of the present invention to enhance the rate of absorption of significant drugs which are rectally administered, from the rectal compartment into the blood stream, is demonstrated with a microenema technique. A male Sprague-Dawley rat weighing 225-250 g. is kept fasting for 16 hours prior to the experiment which is conducted under pentabarbitol anesthesia. During the experiment, the rat is kept on a 38° C. surface. The drug with adjuvant is administered rectally as a 0.3 ml microenema using a 0.01M phosphate buffer at a pH of 7.4 when the depeptide is used as an adjuvant and at a pH of 4.5 when the metabolites of epinephrine are used. Following administration of the drug solution, the rat anus is ligated with thread to avoid leakage of the solution. Blood samples are taken from the jugular vein at regular intervals and centrifuged at 3000 rpm for 10 minutes to provide a plasma sample. The amount of drug absorbed is analyzed as a function of time by appropriate methods, e.g. by high-pressure liquid chromatography. The results of this method show that plasma levels for the various drugs increased significantly after rectal administration in the presence of an adjuvant and relatively high levels were maintained for over 1.5 hours. Following is a table of drug and adjuvant combinations which are evaluated in accordance with the method described above:

| Drug | Adjuvant |
|---|---|
| 1. 4,4'-(3H—2,1-Benzoxathiol-3-ylidene)bisphenol S,S—dioxide (phenol red); | phenylalanyl-phenyl-alanine, 4-hydroxy-3-methoxy-mandelic acid, 3,4-dihydroxy-mandelic acid |

EXAMPLE X

The ability of various of the adjuvants of the present invention to enhance the rate of absorption of significant drugs which are rectally administered, from the rectal compartment into the blood stream, is demonstrated using suppository and microenema formulations. Twelve male beagle dogs weighing 9.5-11 kg. are used and are fasted for 36 hours prior to the experiment. The dogs are divided into three groups of four and crossed over with respect to dosage form. Witepsol H-15 is used as an excipient to prepare with 8% gelatin in saline. Suppositories are administered in the amount of 0.5 g. Microenemas are administered with a volume of 0.5 ml. The formulations may contain varying amounts of adjuvant. Blood samples are taken at intervals from the external jugular vein. Blood samples are heparinized and centrifuged at 4000×G for 10 minutes. The plasma levels of the drugs are analyzed as a function of time using plasma aliquots for the assay of drug concentration. The results of this method show that the inclusion of adjuvant significantly enhanced the bioavailability of the drugs in the blood stream. Following is a table of drug and adjuvant combinations which are evaluated in accordance with the method described above:

| Drug | Adjuvant |
| --- | --- |
| 1. Erythromycin | Sodium 5-methoxy salicylate, sodium salicylate |
| 2. Gentamycin | sodium 5-methoxy salicylate, sodium salicylate |
| 3. MK-421 | sodium 5-methoxy salicylate, sodium salicylate |

EXAMPLE XI

The ability of various of the hydroxyaromatic acid adjuvants of the present invention to enhance the rate of absorption of insulin which is rectally administered from the rectal compartment into the blood stream, is demonstrated using a microenema technique. A male beagle dog weighing 9.5 t 11 kg. is used. Rectal administration of insulin is in the form of a 0.5 ml. or a 0.25 ml. microenema. Insulin microenema formulation are made up in either 0.9% sodium chloride or in 0.9% sodium chloride with 4% gelatin. Blood samples are taken at intervals for the external jugular vein and treated with EDTA. Blood samples are centrifuged at 4000×G for 10 minutes. Plasma glucose levels are determined at 650 nm using the O-toluidine method. Plasma insulin levels are determined using an immunospecific enzyme assay (Toyo Jozo Company, Ltd., Japan). The results of this method show that the presence of the adjuvant caused a significant decrease in plasma glucose levels concomitant with a large increase in plasma insulin levels. Following is a table of drug and adjuvant combinations which are evaluated in accordance with the method described above:

| Drug | Adjuvant |
| --- | --- |
| 1. Insulin | Sodium 5-methoxy salicylate, sodium salicylate |

As already described, the methods of the present invention for enhancing the rate of absorption of drugs from the rectal compartment are useful for a wide range of drugs. Without limiting the broad applicability of the novel methods, there are also pointed out a number of drugs for which the novel methods are particularly useful, thus comprising preferred embodiments of the present invention:

3,7-Dihydro 1,3-dimethyl-1H-purine-2,6-dione (theophylline);
2-(Diethylamino)-N-(2,6-dimethyl-phenyl)acetamide (lidocaine);
3-hydroxy-L-tyrosine (levodopa) (L-Dopa);
Gastrin or pentagastrin
Insulin
Heparin;
MK-421
4,4'-(3H-2,1-Benzoxathiol-3-ylidene)bisphenol S,S-dioxide (phenol red);
Gentamycin or erythromycin

EXAMPLE XII

Preparation of Sodium 2-hydroxy-5-methoxy benzenesulfonate p-Methoxyphenol (12.4 g) was dissolved in chloroform (100 ml) and cooled in ice. Chlorosulfonic acid (11.6 g) was added dropwise to the stirred reaction mixture. The cooling bath was removed after the addition and stirring continued for 24 hours at room temperature. The chloroform was then evaporated off and the residue was vacuum dried to a hygroscopic light brown solid weighing 20.5 g which was 2-hydroxy-5-methoxybenzenesulfonic acid. NMR ($CDCl_3$) and 3.73 (3H, s, $OCH_3$), 6.8–7.2 (3H, m, aromatic H), and 9.86 (2H, broad s, OH and $SO_3H$). IR (film) 3500–2900, 1512, 1470, 1229, 1198, 996, 938 $cm^{-1}$.

The above sulfonic acid (10 g) was dissolved in water (10 ml) and poured into 75 ml of saturated sodium chloride solution. A white solid separated immediately. It was filtered and dried. Crystallization from water gave the pure sodium salt of 2-hydroxy-5-methoxybenzenesulfonic acid (6.6 g).

NMR ($D_2O$) and 3.83 (3H, s, $OCH_3$), 7.05 and 7.33 (3H, multiplets, aromatic). IR (KBr) 3260, 1518, 1440, 1300, 1280, 1240, 1210, 1905, 1045 $cm^{-1}$.

EXAMPLE XIII

The ability of various of the adjuvants of the present invention to enhance or make possible the absorption of polypeptides from the rectal compartment into the bloodstream, is demonstrated by administration of an aqueous microenema to the anesthetized rat. The polypeptides in this experiment were pentagastrin (5 residues) and gastrin (17 residues), both of which are known to elicit increased gastric acid secretion when administered directly into the bloodstream. The stomach of a Sprague-Dawley rat is exposed by abdominal incision and perfused in situ with physiological saline. The perfusate is continuously titrated with sodium hydroxide solution to maintain a static condition of pH 4. The rate of stomach acid secretion is monitored by recording the amount of titrant used with time. The rate of gastric acid secretion is proportional to blood concentration of the stimulating hormone, i.e. pentagastrin or gastrin.

Figure 5:
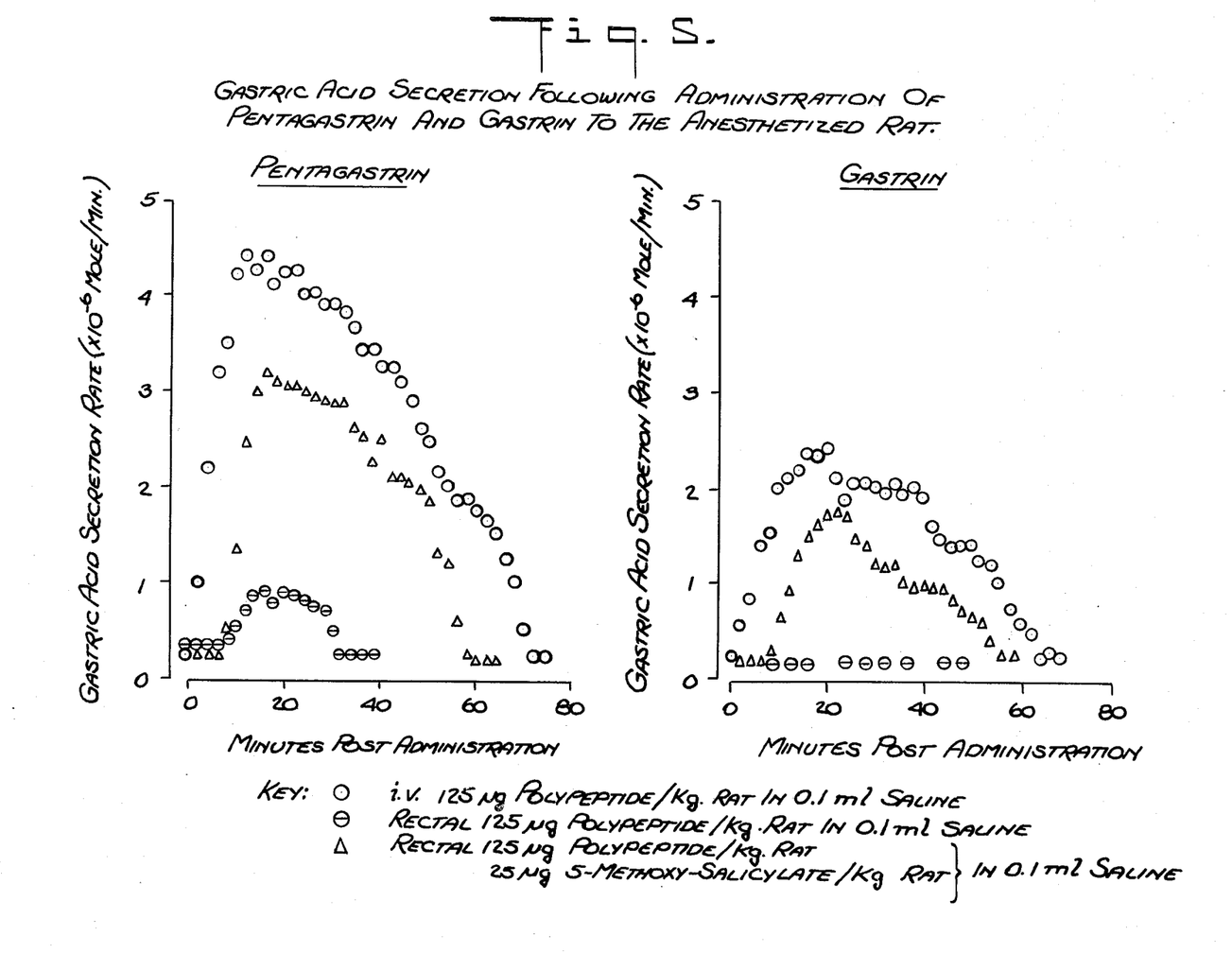
FIG. 5 is a graph illustrating enhanced absorbtion rate of pentagastrin and gastrin by rectal administration when utilizing our method.

Referring to the accompanying graphs and tables, the effects of sodium 5-methoxysalicylate on the relative rate of rectal absorption of pentagastrin and gastrin is shown in FIG. 5 and Table I and II. The pharmacological response to both polypeptides from rectal administration with and without 5-methoxysalicylate is shown. The response from rectal administration is also compared to that from an i.v. administration of the same dose. Tables I and II present cumulative data for several experiments. The effect of 5-methoxysalicylate was to increase rectal absorption of pentagastrin from 6% without adjuvant to 33% with adjuvant. Rectal absorption of gastrin was not observed in the absence of adjuvant, but was estimated to be 18% bioavailable when coadministered with 5-methoxysalicylate.

The adjuvant effect is not limited to 5-methoxysalicylate for rectal delivery of polypeptides. Salicylate has also been shown to enhance rectal delivery of pentagastrin and gastrin in the rat model described above.

Figure 6:
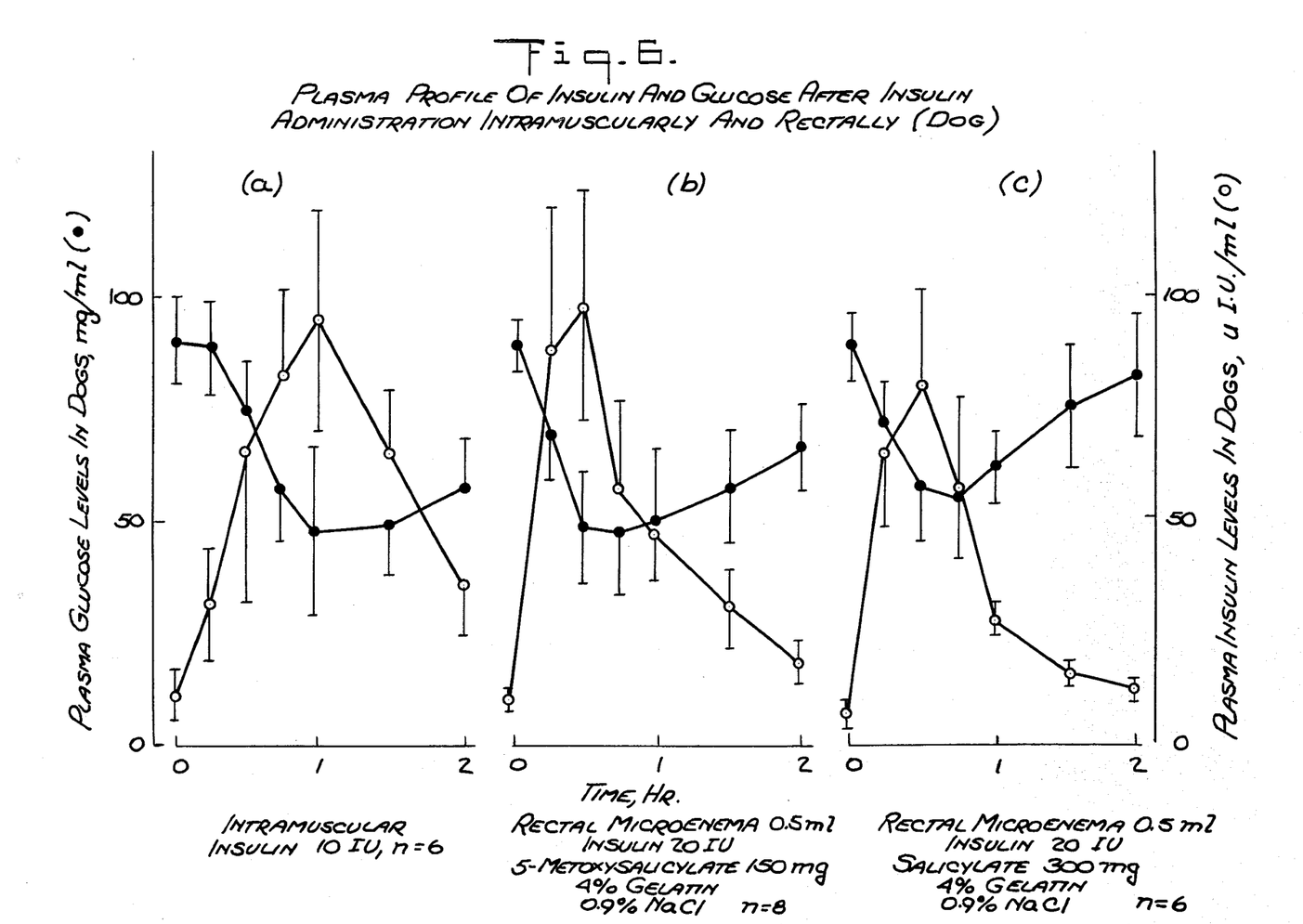
FIG. 6 is a graph illustrating enhanced absorbtion of insulin and glucose.

As an example of a high molecular weight polypeptide, insulin was chosen as the target drug for salicylate enhanced rectal delivery. The animal model is the Beagle dog. Rectal dosage forms (aqueous microenema) are administered to the unanesthetized, unrestrained dog. Blood samples are withdrawn from a peripheral vein and assayed for glucose and insulin concentration. Referring to FIG. 6, the glucose and insulin blood profiles are described after rectal administration with either sodium 5-methoxysalicylate or sodium salicylate. These profiles are compared to those obtained after intramuscular injection of insulin. Although the data is not pictorially represented, rectal administration of an insulin microenema without salicylate caused no change in glucose or insulin blood levels.

TABLE I

Total Amount of Gastric Secretion Stimulated by Pentagastrin
The Amount of Gastric Acid Secreted ($\times 10^{-5}$ mole)

| Experiment No. | iv Administration | | | Microenema 125 g/Kg | |
|---|---|---|---|---|---|
| | 12.5 | 44 | 125 | No adjuvant | Na 5-Meo-Sal |
| 1 | 3.3 | 10.0 | 22.6 | 2.9 | 21.4 |
| 2 | 4.8 | 9.1 | 15.9 | 0.6 | 12.5 |
| 3 | 6.0 | 14.0 | 19.2 | 2.3 | 10.6 |
| 4 | 5.5 | 15.9 | 29.6 | 1.0 | 11.3 |
| 5 | 4.2 | 17.0 | 18.0 | 0.2 | 10.4 |
| 6 | 5.0 | 18.8 | 13.5 | 2.7 | 10.3 |
| mean | 4.8 | 14.1 | 19.8 | 1.6 | 12.9 |
| S.D. | 0.9 | 3.5 | 5.2 | 1.1 | 3.9 |
| Pharmacologic Effect relative to iv | 100% | | | 8% | 65% |
| Bioavailability | 100% (defined) | | | 6% | 33% | dose of pentagastrin ( g/Kg)
§dose of 5-methoxysalicylate (25 mg/Kg)
*based on dose response curve, effect vs. log dose

TABLE II

Total Amount of Gastrin Secretion Stimulated by Gastrin
The Amount of Gastric Acid Secreted ($\times 10^{-5}$ mole)

| Experiment No. | iv Administration | | | Microenema 125 g/Kg | |
|---|---|---|---|---|---|
| | 12.5 | 44 | 125 | No adjuvant | Na 5-Meo-Sal |
| 1 | 3.8 | 6.4 | 7.6 | 0 | 4.6 |
| 2 | 2.8 | 5.6 | 14.1 | 0 | 1.6 |
| 3 | 1.7 | 11.3 | 8.9 | 0 | 7.3 |
| 4 | 2.1 | 8.6 | 14.6 | 0 | 4.6 |
| 5 | 1.4 | 9.5 | 10.4 | 0 | 4.4 |
| 6 | 2.4 | 5.3 | 12.2 | 0 | 6.9 |
| mean | 2.4 | 7.8 | 11.3 | 0 | 4.9 |
| S.D. | 0.8 | 2.2 | 2.6 | 0 | 1.9 |

TABLE II-continued

Total Amount of Gastrin Secretion Stimulated by Gastrin
The Amount of Gastric Acid Secreted ($\times 10^{-5}$ mole)

| Experiment No. | iv Administration | | | Microenema 125 g/Kg | |
|---|---|---|---|---|---|
| | 12.5 | 44 | 125 | No adjuvant | Na 5-Meo-Sal |
| Pharmacologic effect relative to iv | 100% | | | 0.0% | 43% |
| Bioavailability* | 100% (defined) | | | — | 18% | dose of gastrin ( g/Kg)
dose of 5-methoxysalicylate (25 mg/Kg)
*based on dose response curve, effect vs. log dose

EXAMPLE XIV (amino glycoside antibiotics)

The ability of sodium 5-methoxysalicylate to enhance the rectal absorption of gentamycin in the dog is demonstrated by referring to Table VI. Sodium 5-methoxysalicylate is representative of the adjuvant structure claimed in the present invention. Gentamycin is representative of the amino glycoside class of antibiotics. Rectal administration of the best formulation resulted in 45% drug absorption, whereas the same formulation without absorption adjuvant resulted in only 5% drug delivery. The adjuvant effect is also demonstrated to be both concentration and formulation dependent.

TABLE III

Rectal Bioavailability of Gentamycin

| Dosage form and base | Dose of Gentamycin mg/body | Dose of 5-methoxy salicylate mg/body | [AUC]* mg min/mL | Rectal Bioavailability with adjuvant relative to without [AUC]$_p$(dose)$_a$ / [AUC]$_a$(dose)$_p$ | Rectal Bioavailability relative to IV [AUC]$_r$(dose)$_{iv}$ / [AUC]$_{iv}$(dose)$_r$ | n |
|---|---|---|---|---|---|---|
| i.v.-injection | 50 | — | 1254 ± 193 | | | 4 |
| rectal administration | | | | | | |
| suppository | | | | | | |
| Witepsol H-15 | 150 | — | 13 ± 6 | | 0.05 | 4 |
| | 75 | 50 | 313 ± 26** | 47 | 0.17 | 4 |
| | 75 | 75 | 713 ± 72** | 108 | 0.38 | 4 |
| | 75 | 100 | 848 ± 281** | 128 | 0.45 | 4 |
| microenema | | | | | | |
| gelatin gel | 75 | 100 | 357 ± 58** | 54 | 0.19 | 4 |
| | 75 | 150 | 521 ± 82** | 79 | 0.28 | 4 |
| buffer solution | 75 | 150 | 233 ± 61** | 35 | 0.12 | 4 |

*[AUC] = [AUC]$^{120\ min}_{0\ min}$.
**p 0.001 versus rectal administration in absence of adjuvant.

EXAMPLE XV

Figure 7:
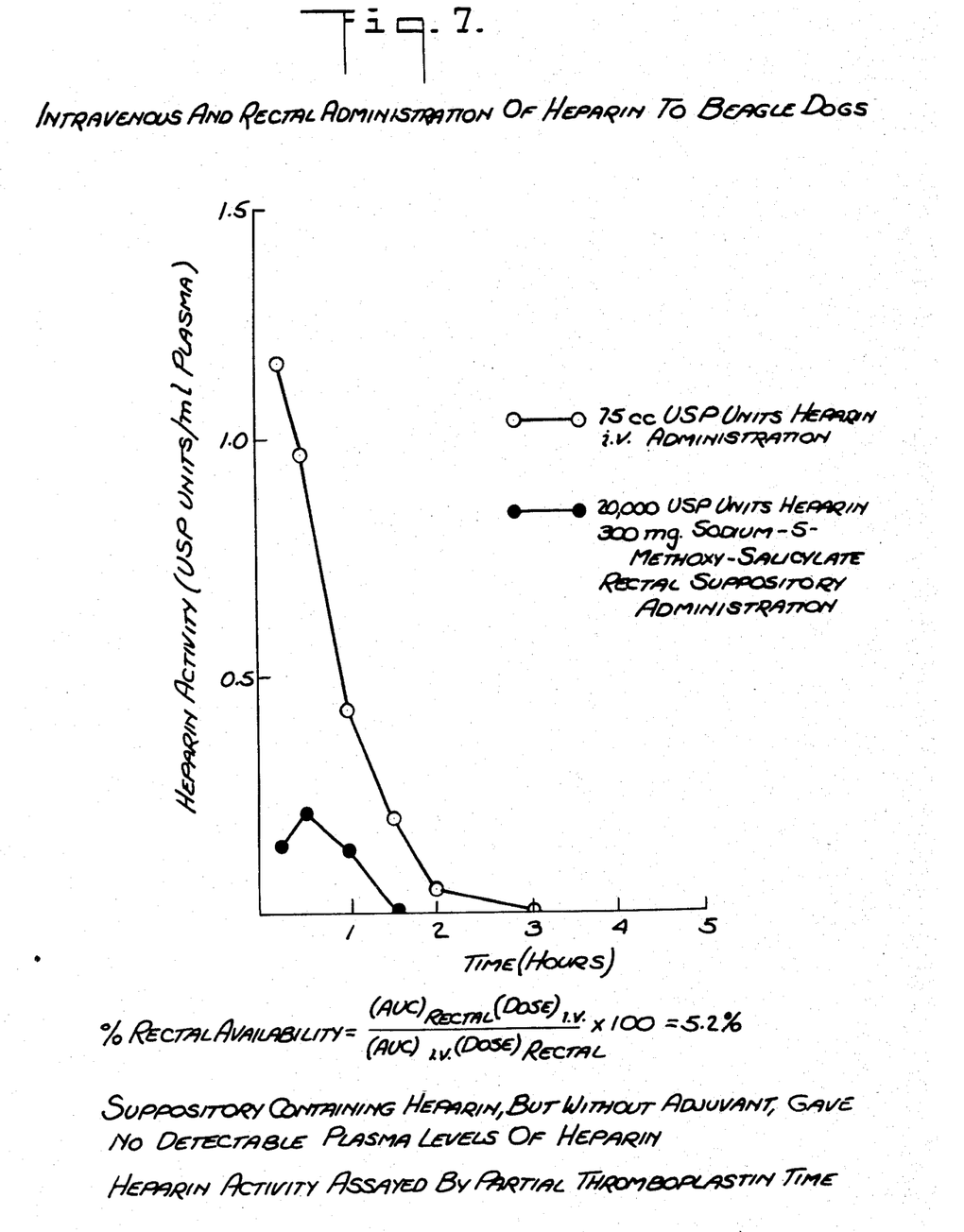
FIG. 7 is a graph illustrating absorption of heparin when utilizing our method.

The ability of the absorption adjuvants of the present invention to enhance the rectal absorption of polysaccharide drug entities such as heparin is demonstrated by referring to the accompanying FIG. 7. FIG. III presents data from the Beagle dog model. Blood levels of heparin were determined using partial thromboplastin time to calculate levels in terms of USP units. Rectal administration of a suppository formulation containing heparin and 5-methoxysalicylate afforded 5% heparin delivery, whereas the same formulation without absorption adjuvant did not produce detectable blood levels of heparin activity. These data demonstrate the ability of the salicylate type adjuvants to facilitate rectal absorption of high molecular weight polysaccharide compounds.

While in the foregoing there has been provided a detailed description of particular embodiments of the present invention, it is to be understood that all equivalents obvious to those having skill in the art are to be included within the scope of the invention as claimed.

What we claim and desire to secure by Letters Patent is:

1. A method for enhancing the rate of absorption of a rectally administered drug from a rectal compartment into the blood stream, said method comprising the steps of preparing a drug form capable of being rectally administered, said drug form comprising a therapeutically effective dosage amount of a drug selected from the group consisting of insulin, pentagastrin and gastrin capable of being absorbed into the blood stream from the rectal compartment and an adjuvant of the formula:

wherein $R_1$ is $CO_2H$, $(CH_2)COOH$, or or a pharmaceutically acceptable salt thereof wherein $R_2$ is OH, H, a lower alkoxy radical, a lower alkyl radical, a halo radical, or a tri-halo lower alkyl radical, and wherein y is an integer of 1 or 2, said adjuvant being present in said drug form in a sufficient amount to be effective in enhancing said absorption rate, and administering said drug form into said rectal compartment.

2. The method of claim 1 wherein said adjuvant is 5-methoxysalicylic acid, salicylic acid, 2,5-dihydroxybenzoic acid; 2,4-dihydroxybenzoic acid; 3-methylsalicylic acid; 5-methylsalicylic acid; 5-tert-octylsalicylic acid; 3-tert-butyl-6-methylsalicylic acid; 3,5-diisopropylsalicylic acid; 3-tert-butyl-5-methylsalicylic acid; 5-bromosalicylic acid, 3,5-dibromosalicylic acid; 5-iodosalicylic acid; 3,5-diiodosalicylic acid; 3,5-diiodosalicylic acid; 2-hydroxyphenylacetic acid; 5-trifluoromethyl-2-hydroxybenzoic acid; 3-methoxysalicylic acid; 5-octyloxysalicylic acid; 5-butoxysalicylic acid; 5-chlorosalicylic acid; 2-hydroxy-3-methoxy-benzoic acid; or the sodium salts thereof.

3. The method of claim 1 wherein said adjuvant is salicylic acid and 5-methoxysalicylic acid, or their sodium salts thereof.

4. The method of claim 1 wherein the adjuvant is salicylic acid or sodium salicylate.

5. The method of claim 1 wherein said administering step is carried out at a pH of below 5.5 or above 7.5.

6. The method of claim 1 wherein said drug form is a suppository.

7. The method of claim 6 wherein said suppository comprises a soft elastic gelatin capsule containing said drug and said adjuvant.

8. The method of claim 1 wherein said administering step is accomplished by a microenema.

9. A rectally administered drug form comprising a therapeutically effective dosage amount of a drug selected from the group consisting of insulin, pentagastrine and gastrine capable of being absorbed into the blood stream from a rectal compartment and an adjuvant of hydroxy aryl or hydroxy aralkyl acids or salts, or esters of the formula:

wherein $R_1$ is $CO_2H$, $(CH_2)COOH$, or or a pharmaceutically acceptable salt thereof wherein $R_2$ is OH, H, a lower alkoxy radical, a lower alkyl radical, a halo radical, or a tri-halo lower alkyl radical and, wherein y is an integer of 1 or 2, said adjuvant being present in said drug form in a sufficient amount to be effective in enhancing the absorption rate of said drug from from said rectal compartment into the bloodstream.

10. The drug form of claim 9 wherein said adjuvant is 5-methoxysalicylic acid, salicylic acid, 2,5-dihydroxybenzoic acid; 2,4-dihydroxybenzoic acid; 3-methylsalicylic acid; 5-methylsalicylic acid; 5-tert-octylsalicylic acid; 3-tert-butyl-6-methylsalicylic acid; 3,5-diisopropylsalicylic acid; 3-tert-butyl-5-methylsalicylic acid; 5-bromosalicylic acid; 3,5-dibromosalicylic acid; 5-iodosalicylic acid; 3,5-diiodosalicylic acid; 2-hydroxyphenylacetic acid; 5-trifluoromethyl-2-hydroxybenzoic acid; 3-methoxysalicylic acid; 5-octyloxysalicylic acid; 5-butoxysalicylic acid; 5-chlorosalicylic acid; 2-hydroxy-3-methoxy-benzoic acid; or the sodium salts thereof.

11. The drug form of claim 9 wherein adjuvant is salicylic acid and 5-methoxy salicylic acid, or their sodium salts thereof.

12. The drug form of claim 9 wherein the adjuvant is salicylic acid or sodium salicylate.

13. The drug form of claim 9 wherein said administering step is carried out at a pH of below 5.5 or above 7.5.

14. The drug form of claim 9 wherein said drug form is a suppository.

15. The drug form of claim 14 wherein said suppository comprises a soft elastic gelatin capsule containing said drug and said adjuvant.

* * * * *